United States Patent
Matsumori

(10) Patent No.: US 7,968,549 B2
(45) Date of Patent: Jun. 28, 2011

(54) DIARYLMETHYLPIPERAZINES AS THERAPEUTIC AGENTS FOR VIRAL MYOCARDITIS

(76) Inventor: Akira Matsumori, Minoo (JP)

( * ) Notice: Subject to any disclaimer, the term of this patent is extended or adjusted under 35 U.S.C. 154(b) by 649 days.

(21) Appl. No.: 11/610,911

(22) Filed: Dec. 14, 2006

(65) Prior Publication Data

US 2007/0281947 A1 Dec. 6, 2007

Related U.S. Application Data

(63) Continuation of application No. 11/398,992, filed on Apr. 5, 2006, now abandoned, which is a continuation of application No. 10/520,047, filed as application No. PCT/EP03/06746 on Jun. 26, 2003, now abandoned.

(30) Foreign Application Priority Data

Jul. 2, 2002 (JP) .................................. 2002-193896
Jul. 2, 2002 (JP) .................................. 2002-193901

(51) Int. Cl.
    *A61K 31/495* (2006.01)
(52) U.S. Cl. .................................................. 514/252.12
(58) Field of Classification Search ............... 514/252.12
    See application file for complete search history.

(56) References Cited

FOREIGN PATENT DOCUMENTS

| GB | 2311940 A | 10/1997 |
| GB | 2324242 A | 10/1998 |
| WO | 9810764 A | 3/1998 |
| WO | WO 9932125 | * 7/1999 |

OTHER PUBLICATIONS

Konig et al (Clinical and Experimental Allergy, vol. 27, Suppl. 2, pp. 33-37; 1997).*
Goren et al (International Journal of Cardiology, vol. 76, pp. 165-172; 2000).*
University of Nebraska Medical Center (UNMC) ([online], www.unmc.edu [retrieved on Feb. 25, 2009]. From the Internet: <URL: http://www.unmc.edu/dept/pathology/enteroviruslab/index.cfm?conref=5).*
Dennert et al. (European Heart Journal, vol. 29, pp. 2073-2082; 2008).*
Huang et al. (Pediatr Cardiol, vol. 19, pp. 498-500; 1998).*
Liu, et al, Viral Myocarditis: Balance Between Viral Infection and Immune Response:, Canadian Journal of Cardiology Pulsus Group, Inc, vol. 10, No. 12, Oct. 1, 1996, pp. 935-943.
Bernheim, J, et al, "Cetririzine: More Than an Antihistamine?", New Drugs for Asthma Therapy, 1991, pp. 269-293.

* cited by examiner

*Primary Examiner* — Phyllis G Spivack
*Assistant Examiner* — Nelson C Blakley, III
(74) *Attorney, Agent, or Firm* — McDonnell Boehnen Hulbert & Berghoff LLP

(57) ABSTRACT

To provide a therapeutic agent for viral myocarditis and viral myocarditis-related viral diseases by treating the occurrence of cell damage in various organs regardless of the type of virus. A therapeutic agent for viral myocarditis and viral myocarditis-related viral diseases is provided that has as an active ingredient 2-[4-(dipehnylmethyl)-1-piperazinyl]-acetic acid, amide derivative, individual optical isomer or pharmaceutically acceptable salt thereof.

5 Claims, No Drawings

DIARYLMETHYLPIPERAZINES AS THERAPEUTIC AGENTS FOR VIRAL MYOCARDITIS

The present invention relates to a prophylactic or therapeutic agent for viral myocarditis or viral diseases related to viral myocarditis (or induced by viral myocarditis), and an ameliorant or prophylactic for viral cell damage, comprising as an active ingredient, 2-[4-(diphenylmethyl)-1-piperazinyl]-acetic acid or amide derivative, an individual optical isomer or a pharmaceutically acceptable salt thereof.

Although virus vaccines have mainly been used for prevention of viral diseases in the past, since vaccines are typically specific to each respective virus, they are only effective against their respective corresponding viruses. However, since there are numerous types of viruses, vaccines are currently used practically for only an extremely limited number of viruses. In addition, since viruses have numerous mutant strains, there are many cases in which a vaccine may not be effective even against the same virus. Moreover, it is extremely difficult to develop a large number of vaccines having minimal adverse side effects.

On the other hand, although various antiviral agents have also been developed (including aciclovir, gancilovir and vidarabine (Ara-A)) and are used practically, these are only effective against an extremely limited number of viral infections, and a drug that is effective against a broad spectrum of viral diseases has yet to be found. In addition, these antiviral agents have strong adverse side effects, and are difficult to be used in a wide range of clinical settings. Moreover, although interferon has recently been applied for the treatment of viral hepatitis and so forth, this is frequently associated with the occurrence of fever and other adverse side effects. In addition, although interferon inhibits virus growth, it has not been reported to directly prevent cell damage. Moreover, although gamma globulin is widely used for the treatment of viral diseases, its efficacy has not always been consistent.

As has been described above, since there are numerous types of viruses, it is typically difficult to provide specific treatment for each virus. Thus, it is extremely important to prevent or treat cell damage and so forth in various organs that occurs during numerous viral diseases.

In addition, cell damage is frequently known to accompany viral diseases. In addition to this damage resulting directly from virus growth, various immune reactions are thought to be involved that are brought about by viral infection. It is therefore also extremely important to prevent or treat the cell damage that accompanies viral diseases.

In general, myocarditis is a myocardiopathy based on an inflammatory lesion of the heart muscle, and is classified on the basis of cause into infectious myocarditis caused by viruses or bacteria, and non-infectious myocarditis caused by collagen diseases, sarcoidosis and so forth. Nearly all of the myocarditis normally encountered is caused by a virus, and it is frequently caused by coxsacklevirus, echovirus and herpes simplex virus, and nearly all cryptogenic idiopathic myocarditis is viral in nature. Typically, myocarditis occurs suddenly and although many cases heal completely, there are some cases in which impairment of myocardial function persists for a long period of time.

The clinical symptoms of myocarditis consist of inflammation symptoms and cardiac symptoms, and are quite diverse, ranging from nearly asymptomatic cases to cases resulting in sudden death due to cardiac insufficiency or arrhythmia. In cases of viral myocarditis, symptoms of the common cold, such as fever, coughing and sore throat, as well as gastrointestinal symptoms such as diarrhea and abdominal pain, occur first, followed by the manifestation of a variety of cardiac symptoms such as chest pain, arrhythmia, cardiac insufficiency and Adams-Stokes syndrome within 10 days of onset.

Namely, acute viral myocarditis is strongly suspected in the case a person who has not previously experienced any cardiac abnormalities suffers from cold symptoms such as fever, headache, sore throat and malaise, and gastrointestinal symptoms such as nausea, vomiting, abdominal pain and diarrhea, followed by the manifestation of symptoms such as palpitations, chest pain, dyspnea and bloating, facial pallor, cyanosis, arrhythmia, fainting, frigidity of the peripheral regions of the limbs, joint pain, muscle pain and rash.

When examining a patient thought to have a common cold, although there is the possibility of this occurring as a complication of myocarditis (and particularly viral myocarditis), this disease is considered to be easily overlooked by assuming to be a common cold.

Thus, the development of a drug that allows effective treatment and/or prevention of myocarditis (and particularly viral myocarditis), for which clinical diagnosis is not always easy, and/or its accompanying viral diseases and/or viral cell damage, is extremely significant.

An object of the present invention is to provide a drug that allows prevention or treatment of viral myocarditis to be carried out effectively regardless of the type of virus.

Another object of the present invention is to provide a drug that allows prevention or treatment of viral diseases related to viral myocarditis.

Another object of the present invention is to provide a drug that allows improvement or prevention of viral cell damage.

As a result of earnest research, the inventors of the present invention unexpectedly found that 2-[4-(diphenylmethyl)-1-piperazinyl]-acetic acid or its amide derivative, an individual optical isomer or a pharmaceutically acceptable salt thereof is effective, thereby leading to completion of the present invention. Namely, according to the present invention, there is provided a prophylactic or therapeutic agent for viral myocarditis, comprising as an active ingredient, 2-[4-(diphenylmethyl)-1-piperazinyl]-acetic acid or its amide derivative, an individual optical isomer or a pharmaceutically acceptable salt thereof.

Moreover, the following are also provided by the present invention.

The present invention concerns a prophylactic or therapeutic agent for viral myocarditis-related viral disease, comprising as an active ingredient, 2-[4-(diphenylmethyl)-1-piperazinyl]-acetic acid or its amide derivative, an individual optical isomer or a pharmaceutically acceptable salt thereof.

The present invention concerns an use of a compound selected from 2-[4-(diphenylmethyl)-1-piperazinyl]-acetic acid or amide derivative, an individual optical isomer or a pharmaceutically acceptable salt thereof for the preparation of a medicament intended for preventing or treating viral myocarditis-related viral disease in a patient. More particularly the compound is selected from the group consisting of [2-[4-[(4 chlorophenyl)phenylmethyl]-1-piperazinyl] ethoxy]-acetic acid, its dihydrochloride salt or its levorotatory enantiomer; 2-[2-[4-[bis(4-fluorophenyl)methyl]-1-piperazinyl]ethoxy]acetic acid or its dihydrochloride salt; 5-{4-[(aminocarbonyl) (hydroxy)amino]but-1-ynyl)-2-(2-{4-[(R)-(4 chlorophenyl)(phenyl)methyl]piperazin-1-yl}ethoxy)benzamide or a pharmaceutically acceptable salt thereof; and N-{4-[4-(2-{4-[(R)-(4-chlorophenyl)(phenyl) methyl]-1-piperazinyl}ethoxy)phenyl]-3-butynyl}-N-hydroxyurea or a pharmaceutically acceptable salt thereof.

Usually, the viral myocarditis or virus disease related thereto is caused by RNA virus or hepatitis virus.

Preferably, the RNA virus is orthomyxovirus or picornavirus.

Usually, the viral disease is viral hepatitis (hepatitis A, hepatitis B, hepatitis C, hepatitis E, hepatitis G), adenovirus infection, influenza, herpes infection, viral encephalitis, cytomegalovirus infection, viral enteritis or viral pericarditis.

The present invention concerns also an ameliorant or prophylactic for viral cell damage, comprising as its active ingredient, 2-[4(diphenylmethyl)-1-piperazinyl]-acetic acid or amide derivative, an individual optical isomer or a pharmaceutically acceptable salt thereof.

The following provides a more detailed explanation of the present invention while referring to the drawings as necessary. In the following description, the "parts" or "%" used to represent weight ratio are based on weight unless specified otherwise.

In the present invention, 2-[4-(diphenylmethyl)-1-piperazinyl]-acetic acid or its amide derivative, an individual optical isomer or a pharmaceutically acceptable salt thereof is used as the active ingredient of a prophylactic or therapeutic agent for viral myocarditis.

This 2-[4-(diphenylmethyl)-1-piperazinyl]-acetic acid or amide derivative, an individual optical isomer or a pharmaceutically acceptable salt thereof is described in, for example, EP 0 058 456 and WO 00/58295.

As a preferable example of the above compound and so forth, the 2-[4-(diphenylmethyl)-1-piperazinyl]-acetic acid or its amide is a compound having the following formula (I):

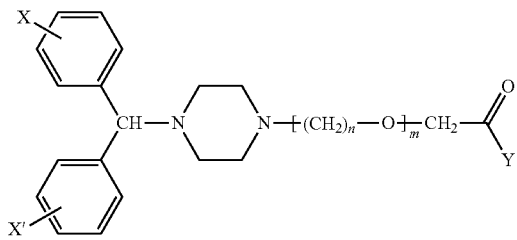

(I)

wherein Y represents a hydroxyl group or an —NH$_2$ group,

X and X' independently represent a hydrogen atom, halogen atom, linear or branched lower alkoxy group or trifluoromethyl group, m represents 1 or 2, and n represents 1 or 2.

A preferable example of a compound within the scope of the compound of formula I is that wherein X and X' are respectively and independently selected from a hydrogen atom, a chlorine atom and a fluorine atom.

Individual preferable examples of the compound of formula I are preferably selected from the following:

2-[2-[4-[(4-chlorophenyl)phenylmethyl]-1-piperazinyl]ethoxy]-acetic acid or its dihydrochloride;

Potassium 2-[2-[4-[(4-chlorophenyl)phenylmethyl]-1-piperazinyl]ethoxy]-acetate;

2-[2-[4-(diphenylmethyl)-1-piperazinyl]ethoxy]-acetic acid or its dihydrochloride;

2-[2-[4-[(4-fluorophenyl)phenylmethyl]-1-piperazinyl]ethoxy]-acetic acid or its hydrate;

2-[2-[4-[bis(4-fluorophenyl)methyl]-1-piperazinyl]ethoxy]-acetic acid;

2-[2-[4-(diphenylmethyl)-1-piperazinyl]ethoxy]-acetic acid or its dihydrochloride;

2-[2-[4-[(2-chlorophenyl)phenylmethyl]-1-piperazinyl]ethoxy]-acetoamide or its dihydrochloride;

2-[2-[2-[4-1(4-methoxyphenyl)phenylmethyl]-1-piperazinyl]ethoxy]ethoxyl-acetoamide or its dihydrochloride;

2-[2-[2-[2-[4-(diphenylmethyl)-1-piperazinyl]ethoxy]ethoxy]-acetoamide or its dihydrochloride;

2-[2-[2-[4-[(4-chlorophenyl)phenylmethyl]-1-piperazinyl]ethoxy]ethoxy]-acetoamide or its dihydrochloride;

2-[2-[2-[4-(diphenylmethyl)-1-piperazinyl]ethoxy]ethoxy]-acetic acid or its dihydrochloride; and, 2-[2-[2-[4-[(4-chlorophenyl)phenylmethyl]-1-piperazinyl]ethoxy]ethoxy]-acetic acid or its dihydrochloride.

Particularly preferable examples of this type of compound are selected from racemic compounds of 2-[2-[4-[(4-chlorophenyl)phenylmethyl]-1-piperazinyl]ethoxy]-acetic acid, its levorotatory and dextrorotatory enantiomers, and pharmaceutically acceptable salts thereof.

Additional examples of such compounds include compounds in which 2-[4-(diphenyl)-1-piperazinyl]-acetic acid or amide derivative is a compound having the following formula (I'):

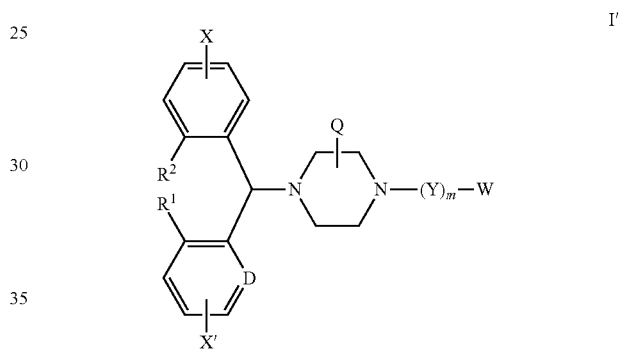

I' wherein X and X' independently represent a hydrogen atom, halogen atom or —(Y')$_{m'}$—W;

D represents —CH= or =N—;

R$^1$ and R$^2$ both represent hydrogen atoms or collectively represent —(CH$_2$)$_2$—;

m and m' independently represent 0 or 1;

Y and Y' represent -L$^1$- or -L$^2$-V(Z)$_t$L$^3$- in which t is 0 or 1;

L$^1$ represents an alkylene, alkenylene or alkynylene, or one of the above in which one or more of the methylene groups is substituted with —O—;

L$^2$ represents (a) an alkylene, alkenylene or alkynylene, or one of the above in which one or more of the methylene groups is substituted with —O— or —N(Q')—, or (b) -L$^4$-CO—N(Q');

L$^3$ represents (a) an alkylene, alkenylene or alkynylene, or one of the above in which one or more of the methylene groups is substituted with —O — or —N(Q")—;

L$^4$ represents an alkylene;

V represents (a) a divalent arene, divalent heteroarene or divalent saturated hetero ring (when t is 0), or (b) a trivalent arene or trivalent heteroarene (when t is 1);

Q represents a hydrogen atom;

Q' and Q" independently represent -AC(O)OR$^6$ or -AC(O)NR$^6$R$^7$;

W and W' independently represent —N(OM)C(O)N(R$^8$)R$^9$, —N(R$^8$)C(O)N(OM)R$^9$, —N(OM)C(O)R$^8$, —C(O)NR$^8$R$^9$ or —C(O)OR$^8$ when at least one of W and W' is —N(OM)C(O)N(R)$^8$R$^9$, —N(R$^8$)C(O)N(OM)R$^9$ or —N(OM)C(O)R$^8$;

Z represents -A'C(O)NR$^{10}$R$^{11}$, -A'C(O)OR$^{10}$, a halogen atom, NR$^3$C(O)R$^4$, NO$_2$, CN or CF$_3$;

A and A' independently represent a direct bond, alkylene, alkenylene, alkynylene or one of the above in which one or more of the methylene groups is substituted with —O—;

M and M' independently represent a hydrogen atom, organic or inorganic anion, pharmaceutically acceptable cation, acyl, alkyl, phosphate, ester acetate, sulfonate, NH$_2$C(O)— or (alkyl)OC(O)— group; and under conditions in which R$^3$, R$^4$, R$^5$, R$^6$, R$^7$, R$^8$, R$^9$, R$^{10}$ and R$^{11}$ independently represent a hydrogen atom or an alkyl group in which one or more of the methylene groups is substituted with —O—; and when one or more of the methylene groups is substituted with —O, —NH, —S, —S(O) or —S(O)$_2$— with the exception of oxygen bound to sulfur in —S(O)— and —S(O)$_2$—, and when one or more of the methylene groups is substituted with =N—, these substitutions do not yield two mutually covalently bonded heteroatoms;

and when m is 0, W represents —C(O)NR$^8$R$^9$ or —C(O)OR$^8$; and, when A is directly bonded in substitution group -AC(O)OR$^6$, R$^6$ does not represent a hydrogen atom), its geometrical isomer, its diastereomer and a pharmaceutically acceptable salt thereof.

A preferable example of a compound within the scope of the compound of formula (I') is that wherein:

X and X' independently represent a hydrogen atom or halogen atom;

Y represents L$^2$-V(Z)$_t$L$^3$- when t is 0 or 1;

L$^2$ represents a C$_1$-C$_6$ alkylene group in which one or more of the methylene groups is substituted with —O—;

V(Z)$_t$ represents a phenylene group that may or may not be substituted with A'C(O)NR$^{10}$R$^{11}$, -A'C(O)OR$^{10}$, halogen, NR$^3$C(O)R$^4$, NO$_2$, CN, CF$_3$, furylene or oxolanylene as desired;

L$^3$ represents a C$_1$-C$_8$ alkylene group in which one or more of the methylene groups may or may not be substituted with —O— or a C$_2$-C$_6$ alkynylene group;

W represents —N(OM)C(O)N(R$^8$)R$^9$, —N(R$^8$)C(O)N(OM)R$^9$ or —N(OM)C(O)R$^8$;

A' represents a methylene or vinylene group; and,

R$^3$, R$^4$, R$^5$, R$^6$, R$^7$, R$^8$, R$^9$, R$^{10}$ and R$^{11}$ independently represent a hydrogen atom or a C$_1$-C$_6$ alkyl group in which one or more methylene groups may or may not be substituted with —O—.

Particularly preferable types of the compound of formula (I') are selected from the following:

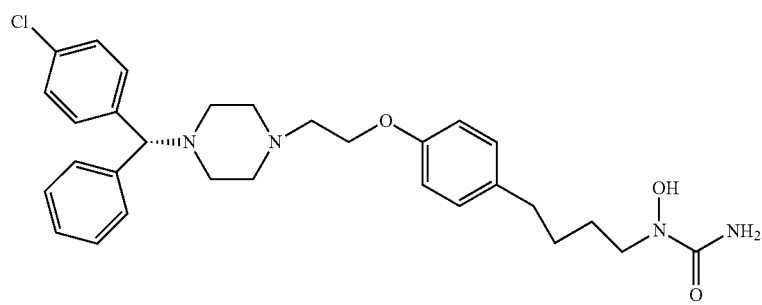

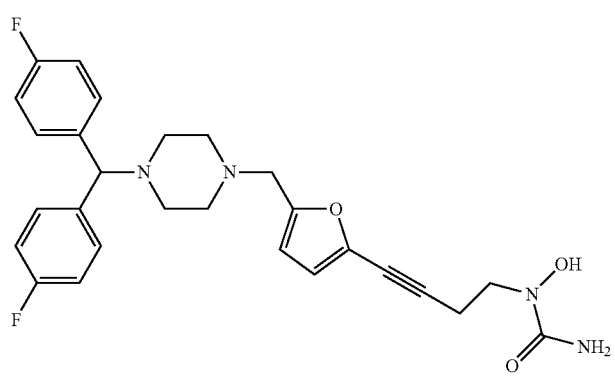

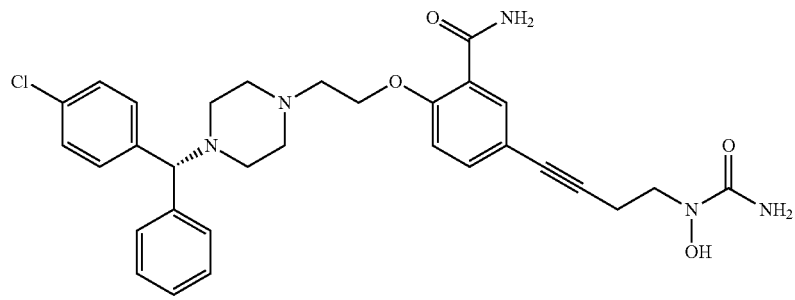

-continued
Chiral
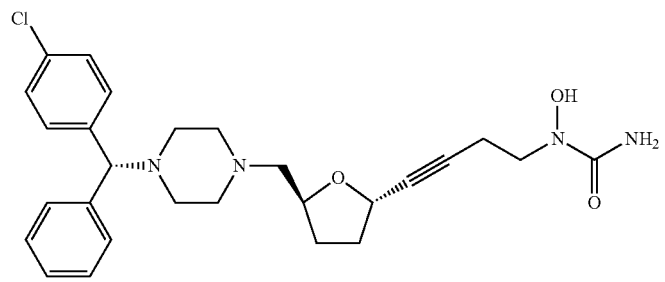
Chiral
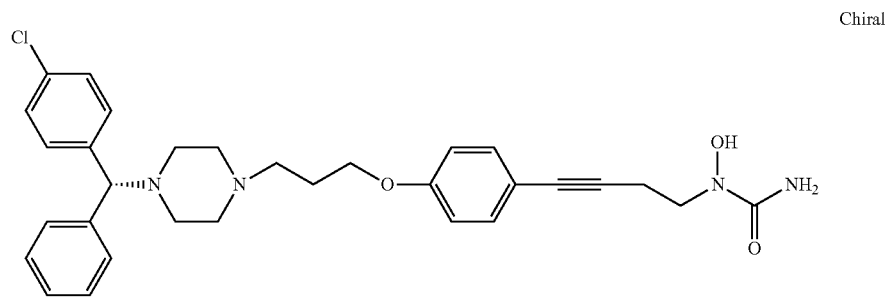
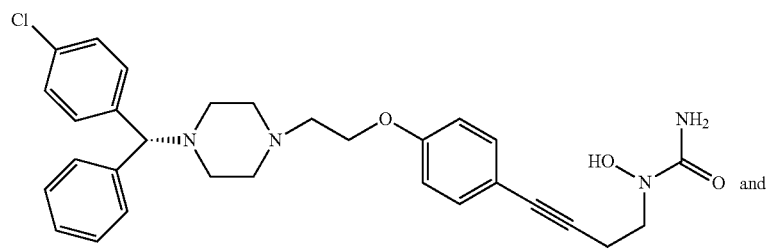
and
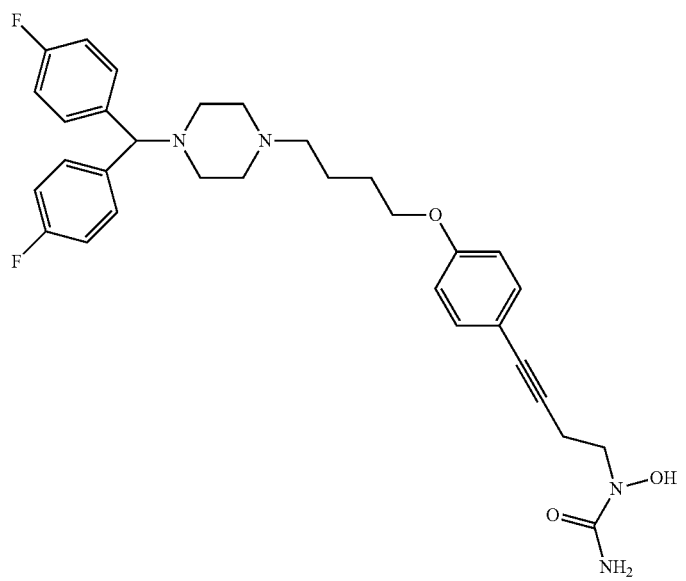

In the present invention, cetirizine, or (±)-[2-[4-[(4-chlorophenyl)phenylmethyl]-1-piperazinyl]ethoxy]acetic acid, which is one mode of the 2-[4-(diphenylmethyl)-1-piperazinyl]-acetic acid or amide derivative, an individual optical isomer or a pharmaceutically acceptable salt thereof, is a compound having the following structural formula:

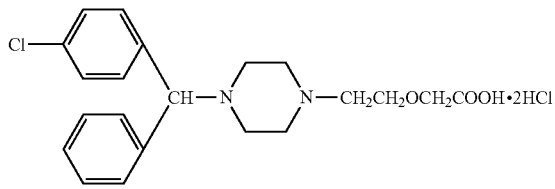

This cetirizine is a known compound and there are no particular restrictions on its production method. Cetirizine can be produced according to, for example, the methods disclosed in the documents indicated below. In the present invention, although cetirizine may be used in its (±) form (namely, as a racemate), the content of either optical isomer may be increased or isolated by optical resolution or other ordinary methods as necessary.

More specifically, the phrase "an individual optical isomer of cetirizine" used here refers to a levorotatory or dextrorotatory enantiomer of cetirizine. More precisely, this refers to that which contains at least 90% by weight (and preferably at least 95% by weight) of one individual optical isomer of cetirizine, and at most 10% by weight (and preferably at most 5% by weight) of another individual optical isomer. The levorotatory enantiomer of cetirizine (since the form of its dihydrochloride salt is levorotatory) is also known as levocetirzine. Each individual optical isomer can be obtained by conventional means (namely, resolution or asymmetric synthesis from a corresponding racemic mixture).

Production processes of cetirizine, its individual optical isomers or its pharmaceutically acceptable salts are described in European Patent No. EP-0 058 146 B1, UK Patents Nos. 2,225,320 and 2,225,321, U.S. Pat. No. 5,478,941, examined European Patent Applications Nos. EP-0 601 028 A1 and EP-0 801 064 A1, and examined International Patent Application No. WO 97/37982.

Cetirizine has been used in the past for allergic rhinitis, eczema and dermatitis, etc. as a sustained selective H1-receptor antagonist (refer to, for example, Yakugyou Jiho Co., Ltd., "Therapeutic Drugs—Collection of Japanese Pharmaceuticals", 1998-1999 edition, page 831).

Although 2-[4-(diphenylmethyl)-1-piperazinyl]-acetic acid, its amide derivative or an individual optical isomer thereof (such as cetirizine) may used in the free state, it may also be in the form of a pharmaceutically acceptable salt as necessary. Although there are no particular restrictions on the method used to form such a salt, as an example of a method that may be used, a pharmaceutically acceptable salt may be obtained by treating with a suitable acid in a suitable solvent. Examples of solvents that may be used at this time include water, methanol, ethanol, diethylether, tetrahydrofuran (THF) and dioxane. Examples of acids that may be used during salt formation include hydrochloric acid, hydrobromic acid, hydroiodic acid, sulfuric acid, nitric acid, phosphoric acid, acetic acid, maleic acid, fumaric acid, benzoic acid, citric acid, oxalic acid, succinic acid, tartaric acid, maleic acid, mandelic acid, methanesulfonic acid, benzenesulfonic acid, p-toluenesulfonic acid and 10-camphorsulfonic acid.

In the present invention, since 2-[4-(diphenylmethyl)-1-piperazinyl]-acetic acid, amide derivative, individual optical isomer or pharmaceutically acceptable salt thereof has low toxicity, it is useful as a prophylactic or treatment agent for viral myocarditis or related viral diseases, and as an ameliorant or prophylactic for viral cell damage, for animals and particularly mammals (including humans, dogs, rabbits, mice and rats).

In the present invention, "myocarditis" refers to a myocardiopathy based on an inflammatory lesion of heart muscle. In addition, "viral myocarditis" refers to infectious myocarditis in which a virus is the agent. This "viral myocarditis" can be distinguished from non-infectious myocarditis caused by collagen diseases or sarcoidosis and so forth as well as infectious myocarditis caused by bacteria and so forth (microorganisms other than viruses) with respect to the following points (documents such as Viral Infection of the Heart, J. E. Banatvala, ed., Edward Arnold Publishers, London 1993, pp. 1-257 can be referred to with respect to this type of distinction).

In the present invention, there are no particular restrictions on viruses that cause viral myocarditis. In addition, there are also no particular restrictions on viruses that cause viral diseases (or viral cell damage) related to viral myocarditis.

Pathogenic viruses that are members of DNA viruses or RNA viruses are included in those viruses that cause viral myocarditis and/or related viral diseases (or viral cell damage). Among such pathogenic viruses, examples of DNA viruses include pox virus, herpes virus (including herpes simplex virus, cytomegalovirus and EB virus), adenovirus and parvovirus.

Examples of RNA viruses among the above pathogenic viruses include reovirus, togavirus, coronavirus, rhabdovirus, paramyxovirus, orthomyxovirus, bunyavirus, arenavirus, retrovirus, picornavirus and calicivirus.

A drug of the present invention can be preferably applied for the prevention or treatment of patients afflicted with viral myocarditis or its related viral diseases caused by an RNA virus or hepatitis virus in particular. Here, examples of RNA viruses to which the drug of the present invention can be particularly preferably applied include orthomyxovirus and picornavirus.

There are no particular restrictions on viral diseases related to viral myocarditis provided they are diseases that are induced by viral myocarditis. Examples of such diseases include viral hepatitis (hepatitis A, hepatitis B, hepatitis C, hepatitis E, hepatitis G), adenovirus infection, influenza, viral pneumonia, viral bronchitis, herpes infection (including herpes simplex, EB virus (infectious mononucleosis) and herpes zoster), polio, AIDS (HIV infection), adult T-cell leukemia (ATL), papilloma, measles, German measles, exanthema subitum, erythema infectiosum, viral encephalitis, viral meningitis, cytomegalovirus infection, mumps, chickenpox, rabies, viral enteritis, viral pericarditis, coxsackievirus infection, echovirus infection, epidemic hemorrhagic fever and Lassa fever.

Moreover, among the previously mentioned viral diseases, a drug of the present invention is particularly preferably applicable to viral hepatitis (hepatitis A, hepatitis B, hepatitis C, hepatitis E, hepatitis G), adenovirus infection, influenza, herpes infection, viral encephalitis, cytomegalovirus infection, viral enteritis and viral pericarditis.

A drug of the present invention is also effective as an ameliorant or prophylactic for viral cell damage. Here, "viral cell damage" refers to necrosis of heart muscle cells, cellular invasive fibrosis and so forth (documents such as Viral Infection of the Heart, J. E. Banatvala, ed., Edward Arnold Publishers, London 1993, pp. 1-257 can be referred to regarding details of this "viral cell damage").

The 2-[4-(diphenylmethyl)-1-piperazinyl]-acetic acid, amide derivative, individual optical isomer or pharmaceutically acceptable salt thereof of the present invention may be used for oral or parenteral administration, and examples of administration methods include inhalation, rectal insertion and local administration. There are no particular restrictions on the drug form of the 2-[4-(diphenylmethyl)-1-piperazinyl]-acetic acid, amide derivative, individual optical isomer or pharmaceutically acceptable salt thereof of the present invention. The 2-[4-(diphenylmethyl)-1-piperazinyl]-acetic acid, amide derivative, individual optical isomer or pharmaceutically acceptable salt thereof of the present invention may be used as, for example, a pharmaceutical composition or preparation (examples of which include powder, granules, tablets, pills, capsules, injection, syrup, emulsion, elixir, suspension and solution).

These compositions or preparations can be obtained by, for example, formulating the 2-[4-(diphenylmethyl)-1-piperazinyl]-acetic acid, amide derivative, individual optical isomer or pharmaceutically acceptable salt thereof of the present invention in accordance with ordinary methods alone or after mixing it with a pharmaceutically acceptable carrier (such as an adjuvant, vehicle, shaping agent and/or diluent) as necessary.

In the present invention, parenteral administration includes, for example, subcutaneous injection, intravenous injection, intramuscular injection, intraperitoneal injection and intravenous infusion.

An injection preparation, such as a sterile aqueous or oily suspension for injection, can be prepared according to known methods in the applicable field by using a suitable dispersant, wetting agent and suspending agent. The sterile preparation for injection may also be a solution or suspension such as an aqueous solution that can be injected aseptically in a pharmaceutically acceptable diluent or solvent for parenteral administration. Examples of applicable vehicles and/or acceptable solvents include water, Ringer's solution and isotonic saline.

Moreover, a sterile non-volatile oil may also be used as an ordinary solvent or suspending solvent. Non-volatile oils include any non-volatile oils such as fatty acids, natural, synthetic or semi-synthetic fatty oils or fatty acids, and natural, synthetic or semi-synthetic mono-, di- and triglycerides.

A suppository for rectal administration can be produced by mixing the drug with a suitable, lowly irritating shaping agent such as cocoa butter or polyethylene glycol that is a solid at normal temperatures, a liquid at the temperature of the intestinal tract and melts in the rectum to release the drug.

Examples of solid administration forms for oral administration include powder, granules, tablets, pills and capsules. The active ingredient compound can be mixed with at least one additive in this type of solid administration form. At this time, examples of additives include sucrose, lactose, cellulose, mannitol, maltitol, dextran, starch, agar, alginates, chitins, chitosans, pectins, tragacanth gum, gum arabic, gelatins, collagens, casein, albumin and synthetic or semi-synthetic polymers or glycerides.

The above solid administration form may also include different additives in the same manner as ordinary drug forms. Examples of these "different additives" include inert diluents, lubricants such as magnesium stearate, preservatives such as parabenzene and sorbic acid, antioxidants such as ascorbic acid, α-tocopherol and cysteine, disintegration agents, binders, thickeners, buffers, sweeteners, flavorings and fragrances. Tablets and pills may also have an enteric coating.

Examples of liquids for oral administration include pharmaceutically acceptable syrups, emulsions, elixirs, suspensions and solutions. These may also include inert diluents (such as water) ordinarily used in the applicable field.

The dose of the drug of the present invention when administered to patients can be determined corresponding to the patient's age, body weight, general health condition, sex, diet, administration time, administration method, excretion rate, drug combinations, and degree of symptoms of the disease for which the patient is being treated at that time in consideration of those and other factors. Since 2-[4-(diphenylmethyl)-1-piperazinyl]-acetic acid, amide derivative, individual optical isomer or pharmaceutically acceptable salt thereof has low toxicity, it can be used safely.

The daily dose of the subject compound, although possibly varying according to the patient's status, body weight, administration route and so forth, is typically about 0.01-150 mg per day, and preferably about 0.1-100 mg per day, in the case of oral administration, or about 0.01-50 mg per day, and preferably 0.01-20 mg, administered by dividing among one, two or three administrations in the case of intravenous injection, when administering as a therapeutic agent to adult patients with viral myocarditis or its related viral diseases.

Although the following clarifies the effects of the present invention using test examples, these are only intended to merely be examples, and the present invention is not limited in any way by them.

EXAMPLE 1

Effect on Survival Rate in a Cardiac Insufficiency Model

A comparative study was conducted on the effect of cetirizine on survival rate in a cardiac insufficiency model induced by EMC (encephalomyocarditis) viral myocarditis in mice.

28-day-old, male DBA/2 mice were divided into three groups, and EMC virus that causes myocarditis was inoculated intraperitoneally to all groups at 1 pfu/mouse (0.1 ml as phosphate-buffered saline (PBS)) (day 0)(pfu means plaque forming unit). The EMC virus used here was acquired from ATCC (American Type Culture Collection, Manassas, Va., U.S.A.), and said EMC virus was used after diluting with PBS.

Following inoculation, a control group given only distilled water to serve as a control (n=10), a cetirizine low dose group to which cetirizine dissolved in distilled water was administered at a dose of 1 mg/kg/day (n=10), and a cetirizine high dose group to which cetirizine dissolved in distilled water was administered at 10 mg/kg/day (n=10), were forcibly fed once a day using a cannula (Wakenyaku Co., Ltd.) for 14 consecutive days.

The survival rates of the above three groups after 14 days were compared according to the Kaplan-Meier method (documents such as StatView, SAS Institute Inc., Cary, N.C., U.S.A. 1988 can be referred to for further details regarding this Kaplan-Meier method).

Data are obtained by analyzing the results obtained above according to the Kaplan-Meier method.

Only one of the animals of the control group (n=10) was alive after 14 days (survival rate: 10%). On the other hand, four of the animals of the cetirizine low dose group (n=10) were alive after 14 days (survival rate: 40%), while five of the animals of the cetirizine high dose group (n=10) were alive after 14 days (survival rate: 50%), and survival rate was observed to be improved concentration-dependently by administration of cetirizine (p<0.05).

EXAMPLE 2

Effect on Histopathological Changes in Heart Muscle in a Cardiac Insufficiency Model A comparative study was conducted on the effect of cetirizine on histopathological changes in heart muscle in a cardiac insufficiency model induced by EMC viral myocarditis in mice.

28-day-old, male DBA/2 mice were divided into three groups, and EMC virus was inoculated intraperitoneally to all groups at 1 pfu/mouse (day 0) in the same manner as Test Example 1.

Following inoculation, similar to Example 1, a control group given only distilled water to serve as a control (n=7), a cetirizine low dose group to which cetirizine was administered at a dose of 1 mg/kg/day (n=10), and a cetirizine high dose group to which cetirizine was administered at 10 mg/kg/day (n=7), were forcibly fed once a day using a cannula in the same manner as Test Example 1 for 5 consecutive days.

After five days, the hearts of the animals were removed, stained with hematoxylin-eosin stain after fixing with formalin, and scored for the two parameters of heart muscle cellular necrosis and inflammatory cellular invasion in the manner described below (documents such as Circulation 1999; 100; 1823-1829 can be referred to for further details regarding this formalin fixation, hematoxylin-eosin staining and scoring). The scores for heart muscle cellular necrosis and inflammatory cellular invasion were evaluated independently by two observers and then averaged. Statistical analysis was performed using the one way analysis of variance (ANOVA) and Fisher's protected least significant difference test (documents such as StatVien, SAS Institute Inc., Cary, N.C., U.S.A., 1998 can be referred to for further details regarding these statistical analysis methods).

0: No lesions
1+: Lesions in 25% or less of heart
2+: Lesions in more than 25% to 50% of heart
3+: Lesions in more than 50% to 75% of heart
4+: Lesions in more than 75% to 100% of heart Data consisting of heart weight, body weight, heart weight/body weight ratio, heart muscle cellular necrosis and inflammatory cellular invasion measured in accordance with that described above is summarized in Table 1 below. Furthermore, the previously described survival rate data and data relating to heart muscle interferon production to be described later are also shown in Table 1.

TABLE 1

|  | Control group (n = 7) | Cetirizine 1 mg/kg/day (n = 10) | Cetirizine 10 mg/kg/day (n = 7) |
|---|---|---|---|
| Heart weight (g) (day 5) | 0.06 ± 0.0009 | 0.07 ± 0.008 | 0.60 ± 0.006 |
| Body weight (g) (day 5) | 11.3 ± 1.4 | 13.0 ± 2.6 | 11.4 ± 2.1 |
| Heart weight/body weight ratio (day 5) | 5.7 ± 0.7 | 5.4 ± 1.1 | 5.1 ± 0.8 |
| Heart muscle cellular necrosis (day 5) | 2.3 ± 1.3 | 1.8 ± 1.0 |  |
| Inflammatory cellular invasion (day 5) | 2.9 ± 0.4 | 2.3 ± 0.8 |  |
| Heart muscle interferon-γ (day 7) | 1.2 ± 0.9 (n = 10) | 2.2 ± 1.0* (n = 10) |  |
| Survival rate (day 14) | 10% (1/10) | 40% (4/10) | 50% (5/10)* |

Mean ± SD
*p < 0.05 vs. control

As shown in Table 1, a trend of diminished inflammatory cell invasion and necrosis was observed more dose-dependently in the cetirizine dose groups in histopathological changes (images) of the heart as well.

Based on the results of the above Examples 1 and 2, cetirizine hydrochloride was clearly shown to be effective against viral infection by improving the mortality rate of mice induced by EMC viral infection and improving viral myocarditis.

Furthermore, the above animal model of distention myocardiopathy is described in Circulation, 65: 1230-1235, 1982 or Circulation, 66: 355-360, 1982.

EXAMPLE 3

Effect on Intramyocardial Cytokine Production in a Cardiac Insufficiency Model A comparative study was conducted on the effect of cetirizine on cytokine production within heart muscle in a cardiac insufficiency model induced by EMC viral myocarditis in mice.

28-day-old, male DBA/2 mice were divided into three groups, and EMC virus was inoculated intraperitoneally to all groups at 1 pfu/mouse (day 0) in the same manner as Example 1.

Following inoculation, similar to Example 1, a control group given only distilled water to serve as a control (n=10), a cetirizine low dose group to which cetirizine was administered at a dose of 1 mg/kg/day (n=10), and a cetirizine high dose group to which cetirizine was administered at 10 mg/kg/day (n=10), were forcibly fed once a day using a cannula in the same manner as Test Example 1 for 7 consecutive days.

After seven days, the ventricles aseptically removed from the mice were weighed and then homogenized (conditions: 0° C., 30 seconds) using an ultrasonic homogenizer (Astrason, product name: Ultrasonic Converter) in PBS (phosphate-buffered saline, 1 ml, pH=7.4) and centrifuged for 20 minutes under conditions of 4° C. and 14,000 rpm followed by using the resulting supernatant as the sample for assaying IL-2, IL-12, IFN-γ and IFN-α.

The protein concentration of each cytokine was measured by ELISA using a commercially available kit (Circulation, 100: 1102-1108, 1999). The ELISA kit for mouse IL-2 and IFN-γ was purchased from the Genzyme Corporation, Cambridge, U.S.A., while the ELISA kit for mouse IL-12 and TNF-α was purchased from Endogen Inc., Cambridge, U.S.A.

The total protein concentration of each supernatant was measured by the bicinchoninic acid (BCA) method followed by calculation of the ratio of cytokine concentration to total protein concentration (J. Am. Coll. Cardiol., 33: 1400-1407, 1999). Each cytokine protein concentration was expressed as pg/mg of total protein or ng/mg of total protein. Statistical analysis was performed in the same manner as Test Example 2 using one way ANOVA and Fisher's protected least significant difference test.

The results of statistical analysis with respect to intramyocardial IFN-γ among the above cytokines are as follows.

Administration of cetirizine was observed to result in a concentration-dependent increase in intramyocardial IFN-γ 7 days after virus inoculation.

As shown in the previously mentioned Table 1, administration of the 2-[4-(diphenylmethyl)-1-piperazinyl]-acetic acid, amide derivative, individual optical isomer or pharmaceutically acceptable salt thereof of the present invention was observed to demonstrate ameliorative effects on viral cell damage. A drug of the present invention exhibits therapeutic efficacy against viral myocarditis or viral myocarditis-related viral diseases, and is also effective for the prevention of said diseases.

According to the present invention as described above, 2-[4-(diphenylmethyl)-1-piperazinyl]-acetic acid, amide derivative, individual optical isomer or pharmaceutically acceptable salt thereof is obtained that is useful as a prophylactic or therapeutic agent for viral myocarditis, prophylactic or therapeutic agent for viral myocarditis-related viral diseases, and/or ameliorant or prophylactic for viral cell damage.

The invention claimed is:

1. A method of treating viral myocarditis in a patient comprising administering to the patient a therapeutically effective amount of [2-[4-[(4-chlorophenyl)phenylmethyl]-1-piperazinyl]ethoxy]-acetic acid.

2. The method of claim 1, wherein said viral myocarditis is due to a picornavirus.

3. The method of claim 2, wherein said picornavirus is an EMC virus.

4. The method of claim 1, wherein said viral myocarditis is due to a hepatitis virus.

5. The method of claim 4, wherein said hepatitis virus is hepatitis C virus.

* * * * *